United States Patent
Pedroso et al.

(10) Patent No.: US 12,226,592 B2
(45) Date of Patent: Feb. 18, 2025

(54) CATHETER DESIGNS FOR ENHANCED COLUMN STRENGTH

(71) Applicant: DePuy Synthes Products, Inc., Raynham, MA (US)

(72) Inventors: Pedro D. Pedroso, Parkland, FL (US); Chadwin Hanna, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/381,758

(22) Filed: Oct. 19, 2023

(65) Prior Publication Data
US 2024/0042171 A1 Feb. 8, 2024

Related U.S. Application Data

(63) Continuation of application No. 17/114,725, filed on Dec. 8, 2020, now Pat. No. 11,826,520.

(51) Int. Cl.
*A61M 25/00* (2006.01)

(52) U.S. Cl.
CPC .... *A61M 25/0052* (2013.01); *A61M 25/0068* (2013.01); *A61M 2205/0222* (2013.01); *A61M 2210/12* (2013.01)

(58) Field of Classification Search
CPC .......... A61M 25/0053; A61M 25/0051; A61M 25/0052; A61M 25/0054; A61M 25/005; A61M 25/0012; A61M 25/0013; A61M 2025/0059; A61M 25/0067; A61M 25/0068

See application file for complete search history.

(56) References Cited

U.S. PATENT DOCUMENTS

| | | | |
|---|---|---|---|
| 4,981,478 A | * | 1/1991 | Evard ................. A61M 25/005 600/585 |
| 5,102,402 A | | 4/1992 | Dror |

(Continued)

FOREIGN PATENT DOCUMENTS

| | | |
|---|---|---|
| EP | 1 707 234 A1 | 10/2006 |
| EP | 3 583 972 A2 | 12/2019 |

(Continued)

*Primary Examiner* — Michael J Tsai
*Assistant Examiner* — Neeraja Gollamudi
(74) *Attorney, Agent, or Firm* — Troutman Pepper Locke LLP

(57) ABSTRACT

The objectives for the designs presented herein can be for a variably flexible and kink-resistant catheter for vascular applications. The designs benefit from good compressive and tensile stiffness. A braided wire support structure can be disposed around an inner liner and an outer layer having a plurality of outer jackets of variable durometer. A metallic reinforcing layer can be cut from a hypotube and be used as the primary structure for catheter stiffness, reducing the reliance on and number of jackets to transition stiffness changes along the length of the catheter. The metallic reinforcing layer can have one or more ribbon cut segments and one or more axial hole patterns laser cut into the hypotube to progressively evolve the stiffness from proximally regions with more column stiffness and distal regions with greater lateral flexibility. The polymer jackets can be reflowed to bond the structure together.

20 Claims, 9 Drawing Sheets

(56) References Cited

U.S. PATENT DOCUMENTS

| | | |
|---|---|---|
| 5,125,909 A | 6/1992 | Heimberger |
| 5,244,619 A | 9/1993 | Burnham |
| 5,403,292 A | 4/1995 | Ju |
| 5,454,795 A | 10/1995 | Samson |
| 5,658,264 A * | 8/1997 | Samson ............... A61M 25/005 604/526 |
| 5,885,508 A | 3/1999 | Ishida |
| 5,897,537 A | 4/1999 | Berg et al. |
| 5,938,587 A | 8/1999 | Taylor et al. |
| 5,947,940 A | 9/1999 | Beisel |
| 6,027,863 A | 2/2000 | Donadio, III |
| 6,221,059 B1 | 4/2001 | Chiang et al. |
| 6,352,531 B1 | 3/2002 | O'Connor et al. |
| 6,391,037 B1 | 5/2002 | Greenhalgh |
| 6,551,239 B2 | 4/2003 | Renner et al. |
| 6,749,560 B1 | 6/2004 | Konstorum et al. |
| 7,722,545 B2 | 5/2010 | Bertsch |
| 7,771,410 B2 | 8/2010 | Venturelli |
| 7,833,203 B2 | 11/2010 | Sherman et al. |
| 7,914,466 B2 | 3/2011 | Davis et al. |
| 8,585,643 B2 | 11/2013 | Vo et al. |
| 9,144,665 B2 | 9/2015 | Salstrom et al. |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,974,926 B2 | 5/2018 | Northrop et al. |
| 10,219,887 B2 | 3/2019 | Johnson et al. |
| 10,617,847 B2 | 4/2020 | Cottone et al. |
| 2002/0087076 A1 | 7/2002 | Meguro et al. |
| 2004/0122415 A1 | 6/2004 | Johnson |
| 2004/0153049 A1* | 8/2004 | Hewitt ............... A61M 25/0012 604/527 |
| 2006/0030835 A1 | 2/2006 | Sherman et al. |
| 2006/0064151 A1 | 3/2006 | Guterman |
| 2006/0264905 A1 | 11/2006 | Eskridge et al. |
| 2007/0255255 A1 | 11/2007 | Shah et al. |
| 2008/0097398 A1* | 4/2008 | Mitelberg ......... A61M 25/0043 604/525 |
| 2008/0188928 A1* | 8/2008 | Salahieh ........... A61M 25/0054 623/2.11 |
| 2008/0281350 A1 | 11/2008 | Sepetka |
| 2010/0063479 A1 | 3/2010 | Merdan et al. |
| 2010/0324649 A1 | 12/2010 | Mattsson |
| 2011/0152765 A1 | 6/2011 | Weber et al. |
| 2012/0101480 A1 | 4/2012 | Ingle et al. |
| 2012/0283768 A1 | 11/2012 | Cox et al. |
| 2013/0046285 A1 | 2/2013 | Griffin et al. |
| 2014/0052108 A1 | 2/2014 | De Kock et al. |
| 2014/0135812 A1 | 5/2014 | Divino et al. |
| 2014/0200607 A1 | 7/2014 | Sepetka et al. |
| 2015/0080858 A1 | 3/2015 | Moss |
| 2015/0231367 A1* | 8/2015 | Salstrom ........... A61M 25/0138 604/95.01 |
| 2015/0258305 A1 | 9/2015 | Dye |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |

(56) References Cited

U.S. PATENT DOCUMENTS

| | | |
|---|---|---|
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296221 A1 | 10/2017 | Di Caprio et al. |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0126119 A1 | 5/2018 | McNiven et al. |
| 2020/0222664 A1 | 7/2020 | Cottone et al. |

FOREIGN PATENT DOCUMENTS

| | | | |
|---|---|---|---|
| JP | 2001-161631 A | 6/2001 | |
| JP | 2012-20068 A | 2/2012 | |
| JP | 2014-236863 A | 12/2014 | |
| KR | 10-2010-0098404 A | 9/2010 | |
| WO | WO-9633763 A2 * | 10/1996 | .......... A61M 25/005 |
| WO | WO 2017/027161 A1 | 2/2017 | |
| WO | WO 2020/055448 A1 | 3/2020 | |
| WO | WO 2020/175462 A1 | 9/2020 | |

* cited by examiner

CATHETER DESIGNS FOR ENHANCED COLUMN STRENGTH

CROSS REFERENCE TO RELATED APPLICATION

The present application is a continuation application of U.S. patent application Ser. No. 17/114,725 filed Dec. 8, 2020. The entire contents of which are hereby incorporated by reference.

FIELD OF THE INVENTION

The present disclosure generally relates to devices and methods for accessing blood vessels during intravascular medical treatments. More specifically, the present disclosure relates to a catheter having improved flexibility while maintaining axial stiffness.

BACKGROUND

Catheters serve a broad range of functions in intravascular medical treatments. Catheters are typically a thin tube manufactured from medical grade materials that can be inserted into a body and can be used to deliver drugs or other devices, perform surgical procedures, remove blockages from vessels, and a variety of other purposes. By modifying the material or adjusting the way a catheter is manufactured, it is possible to tailor different sections of the catheter for particular applications.

It is preferable to have both a small outer diameter and a large inner diameter and lumen for most intravascular catheters. Having a small outer diameter allows the catheter to be maneuvered more easily when inserted into the body, and to be capable of access to more distal sites, such as the neurovascular bed. Having a large inner lumen allows larger medical appliances to be inserted and delivered through the catheter and/or a higher volume of fluid or aspiration to be directed through the inner lumen. To minimize the outer diameter and simultaneously maximize inner lumen volume, it is desirable to have a relatively thin catheter wall thickness that is still capable of having excellent flexibility and good resistance to elongation and compression.

There are a number of access challenges that can make it difficult to access a target site. In cases where access involves navigating the aortic arch (such as with coronary or cerebral blockages) the configuration of the arch in some patients makes it difficult to position a guide catheter. Beyond the arch, accessing the neurovascular bed in particular is challenging with conventional technology, as the target vessels are small in diameter, remote relative to the site of insertion, and are highly tortuous. It is not unusual that a catheter will have to navigate windy pathways with multiple loops, where vessel segment can have several extreme bends in quick succession over only a few centimeters of travel, which can lead to kinking. The ever-narrower reaches of the arterial system can have delicate vessels that can easily be damaged by inflexible or high-profile devices.

Catheters for these procedures can be difficult to design in that they must be fairly stiff at the proximal end to maintain pushability and responsive yet comfortable manipulation for the user, while having the flexibility in more distal portions to endure high flexure strains and progress through loops and increasingly smaller vessel sizes without causing trauma. For these reasons size, kink-resistance, trackability, and flexibility are the key design parameters usually associated with catheters used in these procedures and managing the transition from softer to stiffer materials and regions is critical to successful patient outcomes.

Several designs and methods have been proposed for getting a catheter to a target site. In one method, the catheter fits over and is slid along a guidewire which is used to gain access to a target site. A thin guidewire, however, almost always has more reach and distal flexibility than the catheter tube. Newer designs have been proposed which utilize various methods to alter the stiffness between the proximal and distal portions of the catheter, such as sets of polymer tubing, often with braids or windings involving wires or bands of other materials for reinforcement. Currently, most of these catheters control transitions from stiffer materials to softer materials by changing the configuration of the braided member (changing the braid PIC count or coil pitch) or by changing the durometer hardness of the surrounding polymer materials. However, too great of a change in the durometer hardness between adjacent polymer segments can create a kink point at the transition. Therefore, current catheter designs are limited to polymer durometer transitions that are similar in value in order to relieve the propensity of kinking at such junctions, leading to a large number of polymer sections which adds cost and manufacturing complexity.

Coils of the braided wires or bands used to reinforce the polymer segments are often a continuous metallic superelastic or stainless steel of very fine size. A sufficiently fine size or diameter of the coils or braids can be prone to kink and difficult to manufacture with the consistency needed for a uniform product. Kinking of the metallic tubular reinforcing layer can add to the risk of the metallic materials cutting into the surrounding polymers at a kink. These materials also add cost and complexity.

Additionally, in thrombectomy procedures, aspiration catheters need to be very flexible to access a remote occlusion, but also benefit from good compressive stiffness (for pushability, and stability and integrity when clot retrieval devices are withdrawn into them) and good tensile stiffness (to avoid stretch and deformation when placed in tension, such as when being retrieved into an outer sheath while holding a large clot). It has been tricky for designers of traditional catheters to combine these characteristics without large trade-offs. Thus, catheter design has often leaned towards sacrificing proximal column strength to gain in flexibility and trackability.

The present designs are aimed at providing an improved catheter construction to address the above-stated deficiencies.

SUMMARY

The innovations of this disclosure involve catheter which have features for controlling the axial and lateral stiffness and stiffness transitions along the length of the catheter shaft. The catheter can be tubular with a proximal end, a distal end, and a longitudinal axis. The catheter can have a low friction inner liner, a braided support structure disposed around the inner liner, a metallic stiffness transitioning reinforcing layer, and a series of outer polymer layers or jackets. The outer jackets can bond the metallic tubular reinforcing layer to the braided wire support structure. Approximate the distal end, a soft polymeric tip can extend from the termination of the braided wire support structure.

The designs can have features which give excellent column strength in the proximal portion of the catheter shaft and transition to an extremely flexible distal section. The metallic reinforcing layer can be configured to balance the stiffness transitions in the catheter. The designs achieve the desired stiffness transitions along the shaft by changing the configuration of these features over different axial segments of the shaft. This transition from softer to stiffer material is key to successful catheter usage in vascular applications.

In some examples, the catheter can be a tube having a proximal end, a distal end, and longitudinal axis. The catheter can be constructed in a series of layers. For example, the catheter can have an inner liner, a braided wire support structure disposed around the inner liner, and a metallic tubular reinforcing layer around the braided support structure configured to give different stiffness properties to at least a portion of the catheter. A plurality of outer polymer jackets can bond the aforementioned structure together. In one example, the catheter can also have a soft polymeric tip extending distally from the termination of the braided wire support structure.

The braided wire support structure can be a number of materials. In one example, the wire is stainless steel. In another example, the wire is Nitinol or some other superelastic alloy. The wire diameter can be approximately 0.0015 inches or some other dimension. Other factors, such as the PIC count of the braid, can be varied to tailor the flexibility of the catheter. A first PIC count in a proximal portion of the braided wire support structure can be different than a second PIC count in a more distal portion of the braided wire support structure. In one example, the first PIC count can be in a range between 20 and 70. In another example, the second PIC count can be in a range between 120 and 200.

The metallic tubular reinforcing layer can be cut from a single continuous hypotube. In one example, the metallic tubular reinforcing layer can extend the full distance between the proximal and distal ends of the catheter. In another example, the metallic tubular reinforcing layer can extend from the proximal end and terminate at some intermediate distance along the braided support structure proximal of the distal end. The metallic tubular reinforcing layer can be divided into an axial series of segments having the same or different cut patterns of removed material configured to give different stiffness properties to at least a portion of the catheter. The cut patterns can be, for example, holes, slots, ribbons, and/or other features cut into the layer. The patterns and density of patterns can vary along axial segments of the catheter.

In some examples, at least one or more axial segments of the catheter can have one or more ribbon cut segments cut in a longitudinally extending spiral around the longitudinal axis. The dimensions and layout of the of the ribbon cut segments can be tailored to better transition changes in stiffness in the various axial segments of the catheter. For example, one or more of the ribbon cut segments can have an axial portion with a first ribbon width different than a second ribbon width of another axial portion of the same ribbon cut segment. In another example, ribbon cut segments can have an axial portion with a first helix pitch different than a second helix pitch of another axial portion of the same ribbon cut segment.

In other examples, one or more of the axial segments can have axial hole patterns cut from the metallic tubular reinforcing layer. In some examples, the hole patterns can have a gradient of varying hole density, where a greater distance between holes means the residual material of the metallic tubular reinforcing layer lends greater column strength to the catheter in those locations. Additionally, the holes of the hole patterns can be of differing diameters and/or shapes, both within a given hole pattern or between two different hole patterns.

The hole patterns can also be disposed in a helical spiral pattern around the longitudinal axis. The helix pattern can have a variable pitch so that more or less bare metal can be present in certain axial portions of the metallic tubular reinforcing layer. In one example, a helical spiral pattern of holes can have an axial portion with a first helix pitch different than a second helix pitch of another axial portion of the helical spiral pattern. In another example, a helical spiral pattern can have an axial portion with a first helix angle different than a second helix angle of another axial portion of the helical spiral pattern.

By varying the pitch and helix angle, no column strength is sacrificed in the axial direction since the metallic reinforcing layer remains solid throughout. These changes to the hole pattern also mean a gradient of removed material is achieved. In some examples, a plurality of tiers of hole pattern types of decreasing/increasing size can be utilized to make the stiffness transitions in the catheter even smoother.

In one example, a catheter for vascular access can have a proximal end, a distal end, and a longitudinal axis extending therebetween. The catheter can have a braided wire support structure disposed around an inner liner, a metallic tubular reinforcing layer, and one or more outer polymeric jackets.

In some examples, the braided wire support structure can extend from the proximal end of the catheter to some point approximate the distal end. The braid itself can feature a single PIC count or can have variable PIC counts in different axial portions of the catheter. The braid can also have different braid angles to change flexure properties along the axis of the catheter shaft.

The metallic tubular reinforcing layer can be disposed around the braided wire support structure. The metallic tubular reinforcing layer can extend the full length of the wire support structure, or from the proximal end to some fraction thereof. In some examples, the metallic tubular reinforcing layer can be formed from a single hypotube of a shape memory alloy, stainless steel alloy, or other suitable material.

At least a proximal portion of the metallic tubular reinforcing layer can have one or more axial hole patterns having a gradient of varying hole density cut into the layer. In one example, the hole patterns can be disposed in a helical spiral pattern around the longitudinal axis. In another example, the gradient can be achieved by varying the diameter and/or spacing of the hole patterns, which can be straight axial geometry or a helical spiral pattern.

In another instance, the metallic tubular reinforcing layer can have a portion with one or more ribbon cut segments configured in a longitudinally extending spiral around the longitudinal axis. Similar to other examples, the ribbon cut segments can have design variables, such as ribbon width and pitch, which can be varied along the axial length of the segments to adjust the stiffness contribution of the metallic tubular reinforcing layer. The helix angle of the coils of the ribbon relative to the axis can also be tailored for this purpose.

The transition from, for example, one axial hole pattern to another hole pattern, or from a hole pattern to an adjacent ribbon cut segment, can result in stress concentrations and potential kink points. To avoid kinking and blend the stiffness transition between the various hole patterns and ribbon cut segments, the metallic reinforcing layer can also contain transition features at and around the interface of adjacent axial segments. In some examples, the transition feature can be intermediate transition holes to blend the progression from a hole pattern to a ribbon cut segment. In other examples, a slot can be cut into the ribbon to bridge the shift from one ribbon cut segment with certain dimensions to another ribbon cut segment with differing dimensions.

In another example, the one or more outer polymer jackets can be disposed around the metallic tubular reinforcing layer. At least one outer polymer jackets can have a durometer hardness different than the durometer hardness of an adjacent polymer jacket to adjust and transition the axial stiffness and flexure properties in different portions of the catheter. For example, the outer jackets can have varying durometer hardness to create a proximal portion with more column stiffness and a distal portion with more lateral flexibility. The jackets can be reflowed over the underlying structure to bond the metallic tubular reinforcing layer to the braided wire support structure. The polymers of the jackets can flow through the holes of the one or more axial hole patterns and gaps in the ribbon cut segments of the metallic reinforcing layer when heat is applied.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings. The drawings are not necessarily to scale, emphasis instead being placed upon illustrating the principles of the invention. The figures depict one or more implementations of the inventive devices, by way of example only, not by way of limitation.

DETAILED DESCRIPTION

The objectives for the designs presented herein can be for a variably flexible and kink-resistant elongated catheter shafts for vascular applications. The designs are flexible enough to access remote vessel occlusions but also benefit from good compressive and tensile stiffness. The catheter can have a braided wire support structure serving as a backbone with a low friction inner liner disposed on the interior surface. Outer polymer layers or laminating jackets can cover this assembly.

The concepts entail replacing the proximal most plastic segments of the catheter with a metallic reinforcing shaft incorporating a tapered cut ribbon segment. In order to make this component incorporate seamlessly with the other plastic and braid components of the overall catheter design, progressive hole and/or slot patterns can be placed in the proximal portion of the metal shaft (proximal to the ribbon segment). This allows for a plastic jacket or jackets to be placed over the entire metal reinforcing shaft and braided structure. The seamless transition can be achieved by tapering the patterns of holes, ribbons, and/or slots in the metallic reinforcing layer without sacrificing axial column strength by maintaining a solid hypotube throughout.

While the description is in many cases in the context of mechanical thrombectomy or other treatments in the neurovascular bed, the devices and methods described may be easily adapted for other procedures and in other body passageways where a catheter with a highly adaptable stiffness requirement is needed. For example, microcatheters typically having a much smaller diameter than other catheters can also be made using these concepts.

Accessing the various vessels within the vasculature, whether they are coronary, pulmonary, or cerebral, involves well-known procedural steps and the use of a number of conventional, commercially available accessory products. These products can involve angiographic materials, rotating hemostasis valves, and guidewires as widely used in laboratory and medical procedures. Though they may not be mentioned specifically by name, when these or similar products are necessarily employed in conjunction with the system and methods of this invention in the description below, their function and exact constitution are not described in detail.

Specific examples of the present invention are now described in detail with reference to the Figures, where identical reference numbers indicate elements which are functionally similar or identical.

Figure 1:
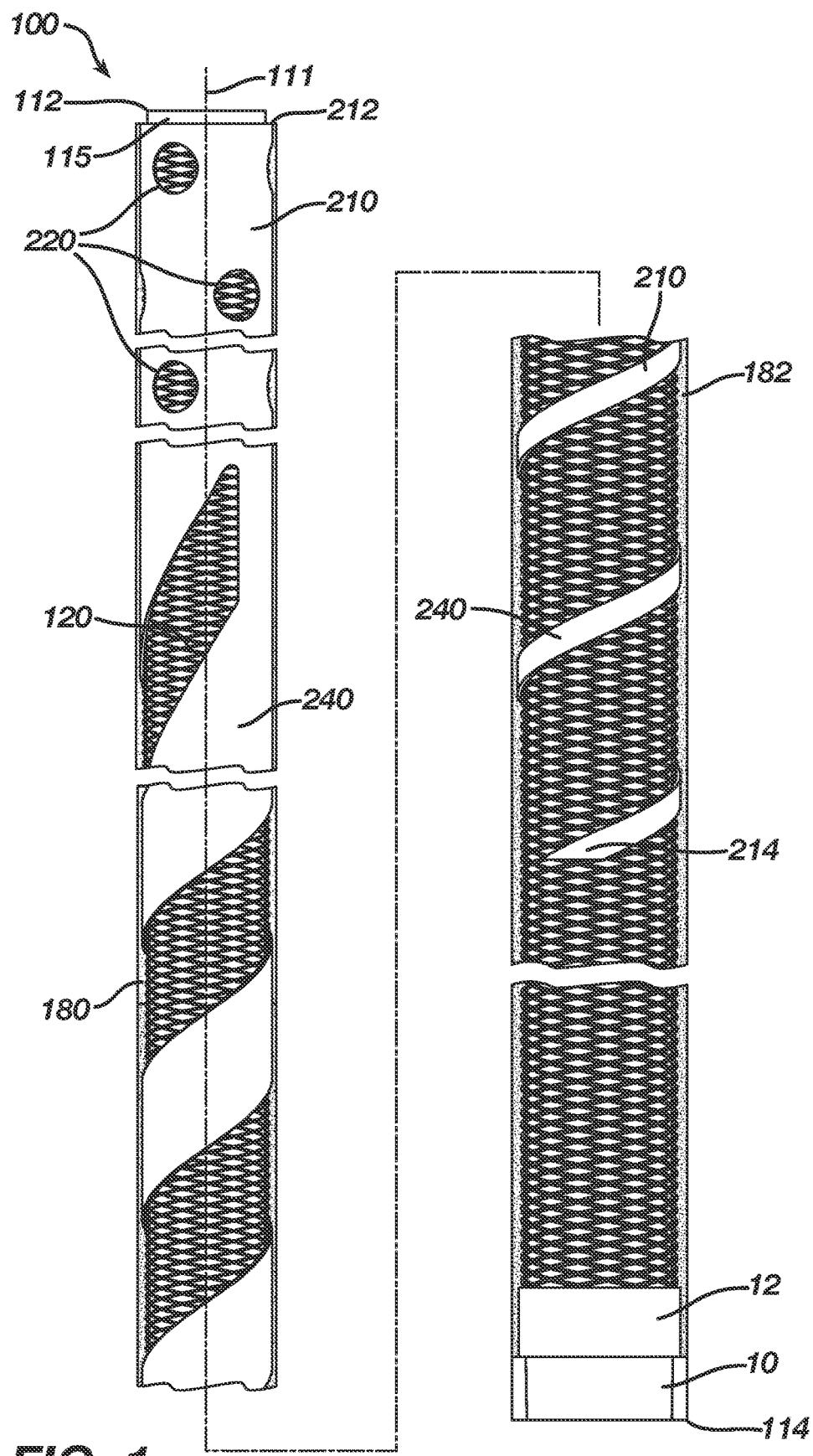
FIG. 1 is a view of a catheter which has a metallic tubular reinforcing layer for enhanced column strength according to aspects of the present invention.

Turning to the figures, in FIG. 1 there is illustrated a catheter 100 for use in intravascular procedures in the vessels of a patient. The support tube 100 can generally be a tubular framework of layered construction between a proximal end 112 and a distal end 114 with a longitudinal axis 111 extending therethrough. The innermost layer can be an inner liner 115 of PTFE or other low friction material to facilitate the passage of ancillary devices through the catheter lumen. Disposed around the inner liner 115 can be a braided wire support structure 120 with braids or windings involving wires or bands of other materials.

Coils of the braid can be continuous metallic super-elastic or stainless steel wires of very fine size. Stiffness transitions can partially be managed by changing the configuration of the support structure 120 (for example, changing the braid PIC count, wire diameter, or coil pitch). For example, a PIC count in a proximal portion of the braided wire support structure 120 can be less than a second PIC count in a more distal region. In one instance, a PIC count of 120-170 can be used in proximal areas of the support structure 120 for good pushability characteristics. In another example, a first PIC count in one region can be in a range between 20-70, while a second PIC count in a more distal region can range between 120-200.

Running at least a portion of the length of the braided wire support structure 120 from the proximal end 112 of the catheter 100 can be a metallic tubular reinforcing layer 210. The metallic tubular reinforcing layer 210 can be, for example, cut from a single continuous hypotube of NiTi or another suitable alloy. Stiffness transitions along the axial length of the catheter 100 can be managed by cutting progressive axial hole patterns 220 and/or ribbon spiral segments 240 along various lengths of the hypotube to tailor flexibility. The metallic tubular reinforcing layer 210 can be a replacement for the proximal portion of many current catheter shaft designs, which are plastic. The metallic tubular reinforcing layer 210 can extend from a proximal end 212 to a distal end 214 which can terminate at some point proximal of the distal end 114 of the catheter 100. Beyond this termination, the inner liner 115 and braided wire support structure 120 can extend distally before the catheter shaft culminates in a soft polymeric tip 10 at the distal end 114. A radiopaque marker or band 12 (such as platinum) can be employed adjacent to the tip 10 to mark the terminal end of the catheter 100 during a procedure.

Similar to many current designs, the catheter can retain a braided wire support structure as a backbone and add the metallic tubular reinforcing layer 210 overlaid. The use of the metallic tubular reinforcing layer 210 can allow a finer gage wire to be utilized in the braid. In some examples, the braid wire diameter can be approximately 0.0030 inches. In other examples, a finer wire of 0.0015 inches can be utilized. The braided support 120 backbone can also be covered by an axial series of plastic tubular jackets 180, 182. The jackets can be made of various medical grade polymers, such as PTFE, polyether block amide (Pebax®), or Nylon. Materials can be chosen, for example, so that more progressively more proximal segments are generally harder and less flexible (by durometer hardness, flexure modulus, etc.) as the proximal end 112 of the catheter 100 is approached.

Figure 2:
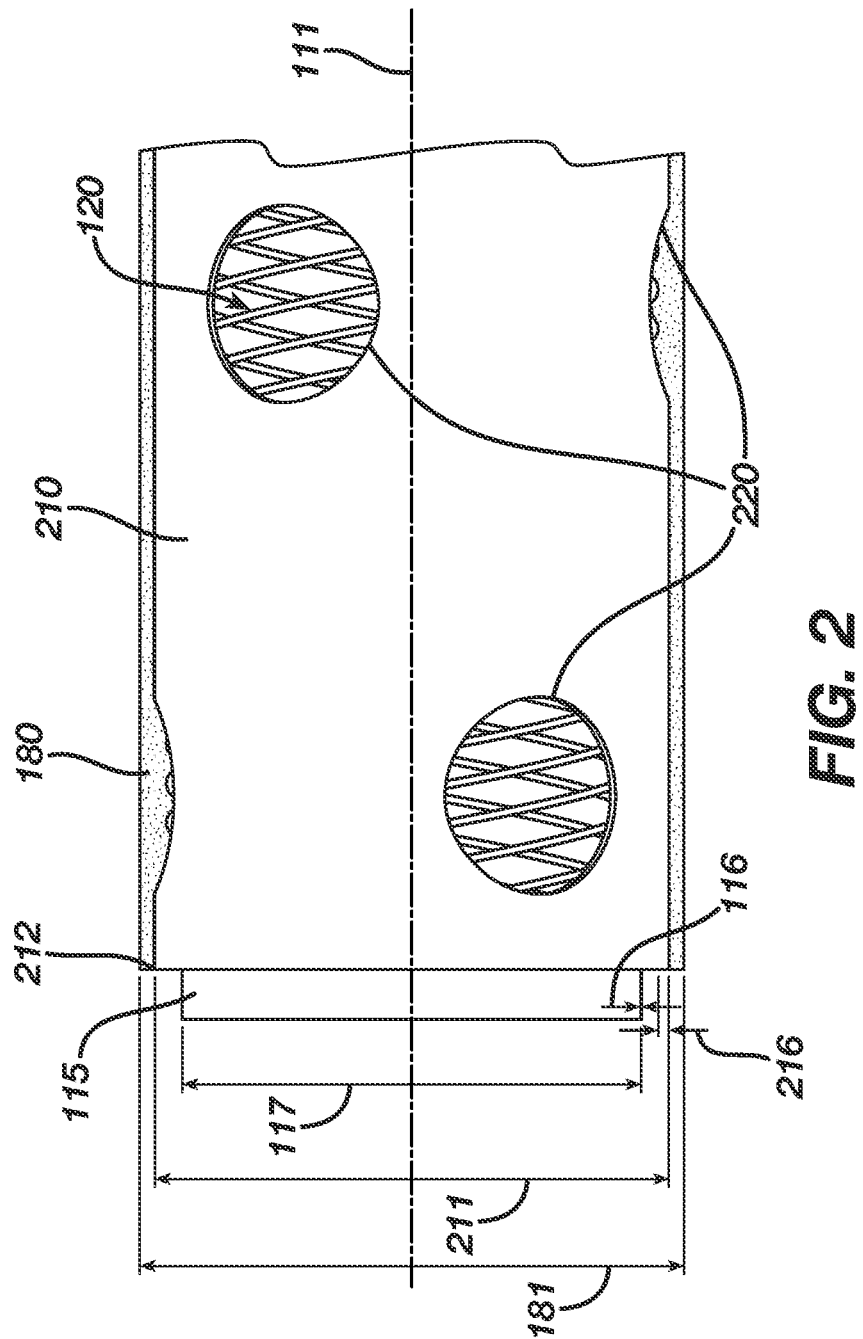
FIG. 2 shows closer view of the proximal end of the catheter of FIG. 1 according to aspects of the present invention.

An enlarged view of a proximal portion of the catheter 100 from FIG. 1 is shown in FIG. 2. The inner liner 115 can have an outer diameter 117 defining the inner lumen of the catheter around the longitudinal axis 111. The outer diameter 117 of the inner liner 115 can be bonded to the inner surface of the braided wire support structure 120, here visible through an axial hole pattern 220 of the overlaid metallic tubular reinforcing layer 210. The inner liner 115 can have a very limited thickness 116 in order to provide the maximum lumen size for the passage of devices and efficient aspiration.

As shown, the axial hole pattern 220 in a more proximal portion of the metallic tubular reinforcing layer 210 can feature large holes geometrically spaced apart to leave significant solid material remaining between them in the metallic tubular reinforcing layer 210. This arrangement can maintain excellent axial stiffness near the proximal end 212 while a hole pattern 220 or patterns can have features that can transition to less material and more lateral flexibility in more distal portions of the metallic tubular reinforcing layer 210.

The metallic tubular reinforcing layer 210 can be placed over the braided wire support structure 120 as if it were a polymer segment from other catheter designs and reflowed or laminated in place to continue distally as the transition from metallic layers to plastic. In order to best blend the metallic tubular reinforcing layer to the portions of the braided wire support structure 120 and inner liner 115, a first polymer jacket 180 can cover the proximal zones as illustrated in FIGS. 1-2. The first polymer jacket 180 could be a range of materials and hardness depending on the properties of the underlying structures. For example, the first polymer jacket 180 can have a hardness of 55-70 Shore D (55D-70D), which can allow the jacket and metallic tubular reinforcing layer 210 in this region to replace otherwise stiffer 72D-80D polymer segments of existing catheter designs.

Figure 3:
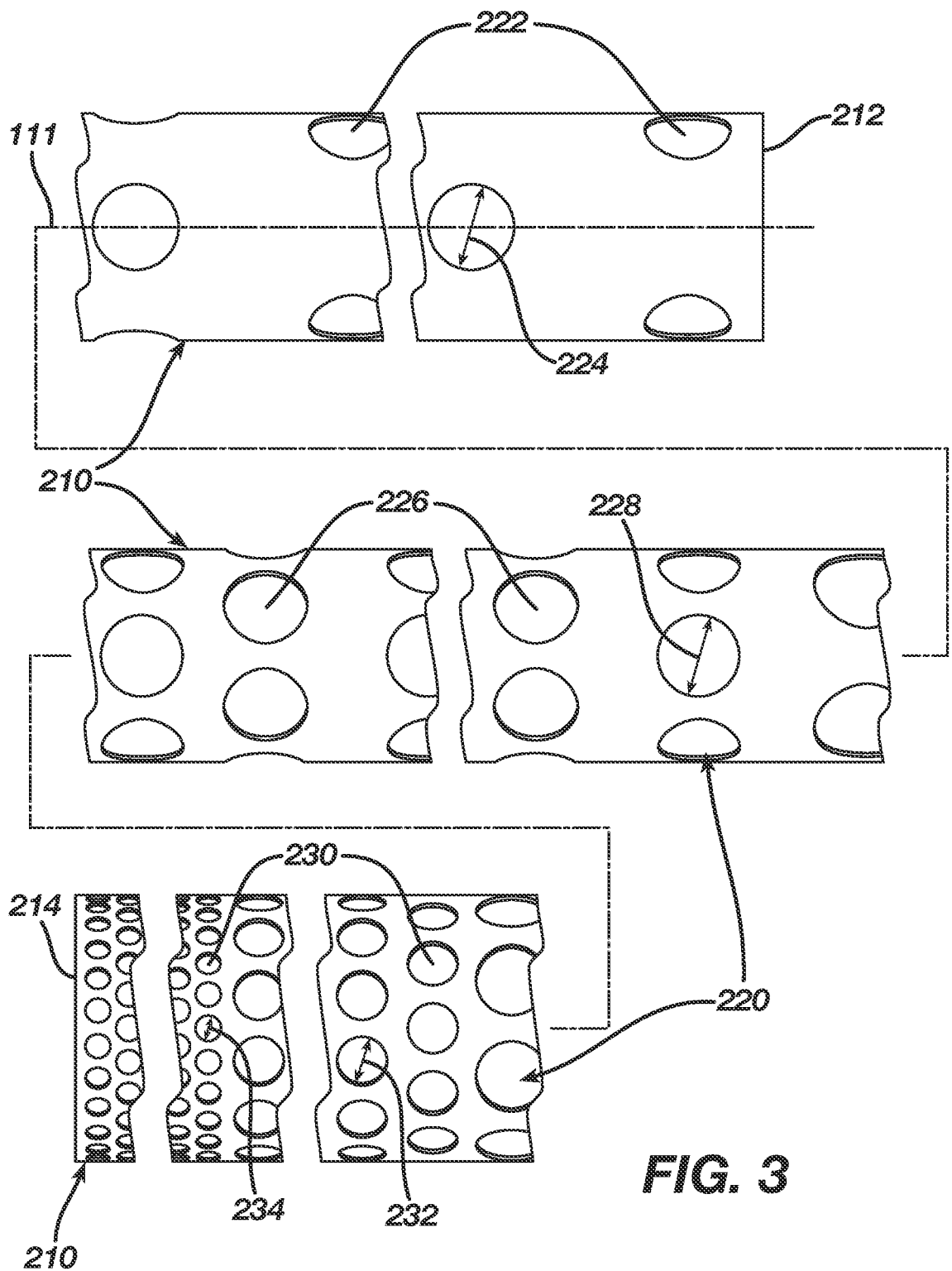
FIG. 3 is a representation of an example of an axial hole pattern for the metallic reinforcing layer according to aspects of the present invention.

The properties of the individual progressive axial hole pattern or patterns 220 of the metallic tubular reinforcing layer 210 can be altered in a variety of ways to achieve the desired flexibility and stiffness transition capabilities. FIG. 3 illustrates an example of a metallic tubular reinforcing layer 210 having a first hole pattern 222 near the proximal end 212 of the layer, a second hole pattern 226 in an intermediate portion of the layer, and a third hole pattern 230 near the distal end 214.

The desired localized stiffness properties of the metallic tubular reinforcing layer 210 can be achieved by changing hole diameter, the number of holes cut in a radial plane, and/or the spacing between the holes for the hole patterns 222, 226, 230. The hypotube of the metallic tubular reinforcing layer 210 shown in FIG. 3, by example and not by limitation, has five different hole diameters, six transition zones, six different hole quantities within a radial plane, and eight different hole spacings. The hole patterns 222, 226, 230 can each have multiple hole sizes and spacings to adjust the stiffness and transition between changes in the pattern along the axial length of the catheter to prevent the formation of kink points.

In one example, the first hole pattern 222 can have holes having a first hole diameter 224. The first hole diameter 224 can be 1.00 mm and the first hole pattern 222 can have three (spaced 120 degrees apart) and/or four holes (spaced 90 degrees apart) within a radial plane. The second hole pattern 226 can have a second hole diameter 228 of 1.00 mm with six holes (spaced 60 degrees apart) within a radial plane. In another case, the second hole pattern 228 can have a second hole diameter of 0.75 mm with 8 holes (spaced 45 degrees apart) within a radial plane, or a combination pattern of these two examples. The third hole pattern 230 near the distal end 214 can have a third hole diameter 232 of 0.50 mm with 12 holes (spaced 30 degrees apart) within a radial plane and a fourth hole diameter 234 of 0.25 mm with 24 (spaced 15 degrees apart) holes within a radial plane, or a combination pattern of these examples.

Designs can have transition patterns or features to bridge the stiffness transition between, for example, the first 222 and second 226 hole patterns. One sample transition zone can thus have a pattern of four 1.25 mm diameter holes per radial plane between the first pattern 222 (four 1.00 mm diameter holes) and second pattern 226 (six 1.00 mm diameter holes). Such a transition pattern can be very brief in axial length but remove an amount of material from the hypotube of the metallic tubular reinforcing layer 210 to ensure the hypotube is has sufficient lateral flexibility in the boundary zone between patterns.

Figure 4:
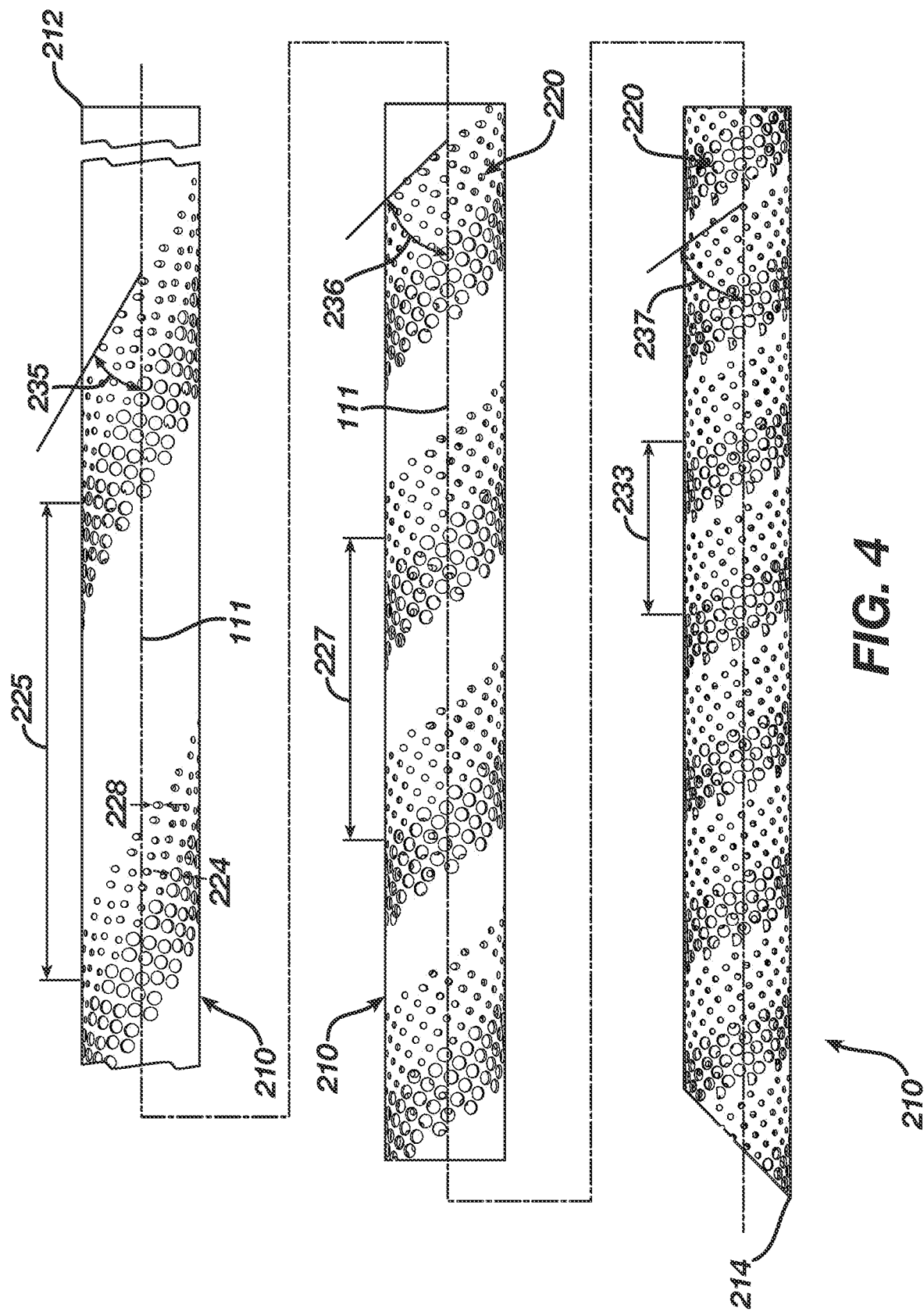
FIG. 4 illustrates an alternative axial hole pattern having a helical configuration according to aspects of the present invention.

In another example, the seamless stiffness transition can be achieved by cutting one or more tapered ribbon or helical patterns of holes into the hypotube of the metallic tubular reinforcing layer 210, as seen in FIG. 4. Similar to other designs, the progressive tapered patterns remove varying amounts of material from the metallic tubular reinforcing layer 210 to allow the gradual move from hard metal to soft plastic in portions of the catheter shaft. Radial flexibility can be gained through the series of holes without sacrificing column strength, since after cutting the hypotube remains solid throughout its construct.

The most flexible distal portion of the hypotube can be obtained by arranging the hole patterns 220 in a dense helix ribbon around the longitudinal axis 111. The hypotube can have a progressive helix pattern as shown in FIG. 4, by way of example and not by limitation, and the pattern can have a "large" first hole diameter 224 and a smaller second hole diameter 228 followed by a band of bare metal. In one example, the first hole diameter 224 can be approximately 0.25 mm ID and the second hole diameter 228 can be approximately 0.15 mm ID. The most flexible distal section can have a relatively short third helix pitch 233 where the hypotube of the metallic tubular reinforcing layer 210 has the least amount of material remaining. The pattern can follow a variable pitch helix proximally where more and more bare metal remains to add axial stiffness and strength. For example, an intermediate portion of the hypotube can have second helix pitch 227 greater than the more distal third helix pitch 233. The proximal end 212 of the metallic tubular reinforcing layer 210 can have a helix pattern with the greatest pitch 225 such that the tube is stiffest around this location.

In another example, the metallic tubular reinforcing layer 210 can have a helical pitch of the hole pattern which varies continuously along the length of the segment hypotube. This configuration can create a constantly changing stiffness profile along the longitudinal length of the metallic tubular reinforcing layer 210.

Similarly, to transition between different sections and pitches, the helix angle of the hole pattern 220 can change along the length of the metallic tubular reinforcing layer 210. For example, a first helix angle 235 approximate the proximal end 212 of the hypotube can be a shallower, more acute angle than more distant portions of the helical hole pattern. As the tube transitions to more distal helix pitches 227, 233, the helix angles 236, 237 can form a progressively more obtuse angle with the longitudinal axis 111.

The rendition in FIG. 4 is a two-tiered hole pattern design. It is anticipated, however, that 3, 4, or even 10 hole types can be used of decreasing/increasing size, or of varying helical patterns, to make the axial stiffness transitions of the catheter even smoother.

The resulting construct can behave largely as a plastic in flexion but maintain the stiffness and strength of metal in the axial direction. In addition, incorporating the metallic reinforcing layer 210 to the catheter construction can have significantly more column strength than existing catheter designs which incorporate only a metal braid or coil at the proximal end. Furthermore, the disclosed designs can have much greater resistance to kinking and will be unable to be crushed on the proximal shaft of the catheter.

Figure 5:
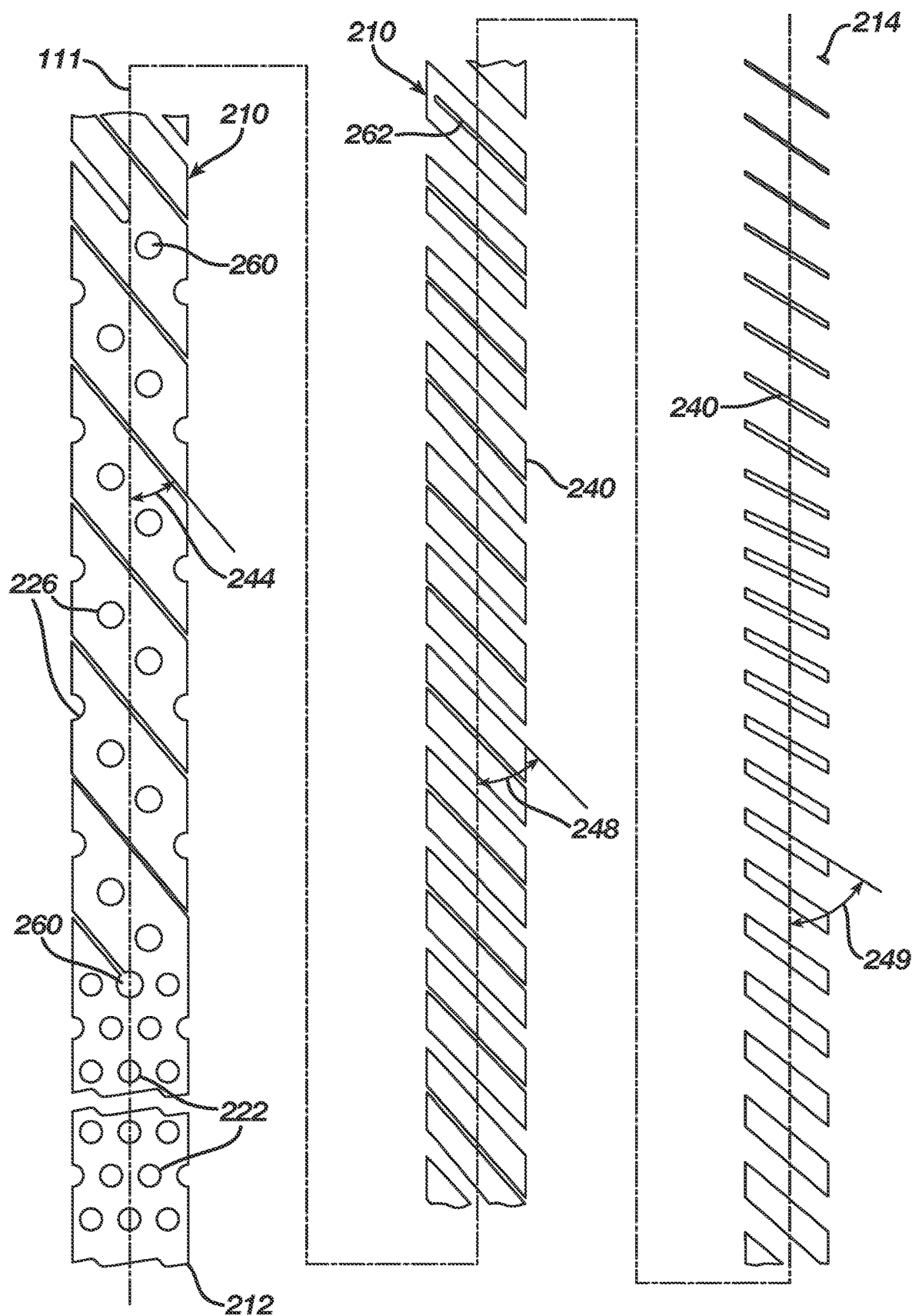
FIG. 5 shows another example of the metallic reinforcing layer according to aspects of the present invention.

Another example of a metallic tubular reinforcing layer 210 incorporating both variable hole patterns and progressive ribbon coil segments to transition shaft stiffness is depicted in FIG. 5. A first axial hole pattern 222 near the proximal end 212 of the metallic tubular reinforcing layer hypotube can transition into a helical second hole pattern 226. The hole patterns can feature holes with the same diameter, different diameters, or a combination of the two. The hole patterns can give way to one or more ribbon cut segments 240 in the intermediate and more distal reaches of the metallic tubular reinforcing layer hypotube 210.

While the hole patterns 222, 226 can be cut variably in a manner similar to that previously described, the ribbon cut segments 240 can also be tailored for stiffness. The ribbon segments 240 can have properties like helical pitch and ribbon width which can be varied continuously along the length of the segment, creating a segmented or constantly changing stiffness profile. Additionally, varied helical angles can be utilized along the length of the tube.

The bending stiffness of the metallic tubular reinforcing layer 210 can further be tailored either by or a combination of varying the cut width and coil width of the ribbon cut segments 240. Where the cut width is kept constant, for instance, the width of a laser beam, the coil width can be varied to tailor bending stiffness. Where the cut width is varied, the coil width can be kept constant or varied and the laser can be used to remove pieces of material. It is appreciated that by using cut width equal to that of the laser beam, no pieces of material are removed, and the cost of manufacture is greatly reduced. On the other hand, by using the laser to remove pieces of material, greater variation in shaft design can be achieved. It is also appreciated that combination of both approaches may be used such that the shaft incorporates more cost-effective cutting/processing means at the proximal end and more costly approaches are kept to a specific distance at the distal end where more complicated cuts can be required to achieve the desired performance.

Additionally, different materials can be used. For example, a proximal section of the shaft may be cut from SS and be joined to a distal section cut from NiTi in order to reduce overall cost while affording the benefits of NiTi to the distal end of the device where it is required for enhance resilience to tight bending curves and also to provide expansion and recovery characteristics. For such a device, the SS and NiTi sections can be joined by welding directly, by welding to a more weldable intermediate metal such as platinum. As an alternative, laser cut interlocking features can hold both cut tubes together in a longitudinal direction. Additionally, an overall change from NiTi to a stiffer material such as SS or Cobalt Chromium can also aide the metal hypotube to overtake the polymer as the main source for catheter stiffness.

The outer jacket or jackets (not shown) can hold the layers together in a radial direction. When refusing the one or more polymeric jackets over the catheter subassembly, the polymer can melt into the holes and the gaps between the slots and ribbon coils to physically connects the metallic tubular reinforcing layer 210 to the metal braided component underneath. The metallic tubular reinforcing layer 210 then allows for the best transitions to the more flexible distal portions of the catheter which have other polymeric components.

Figure 6:
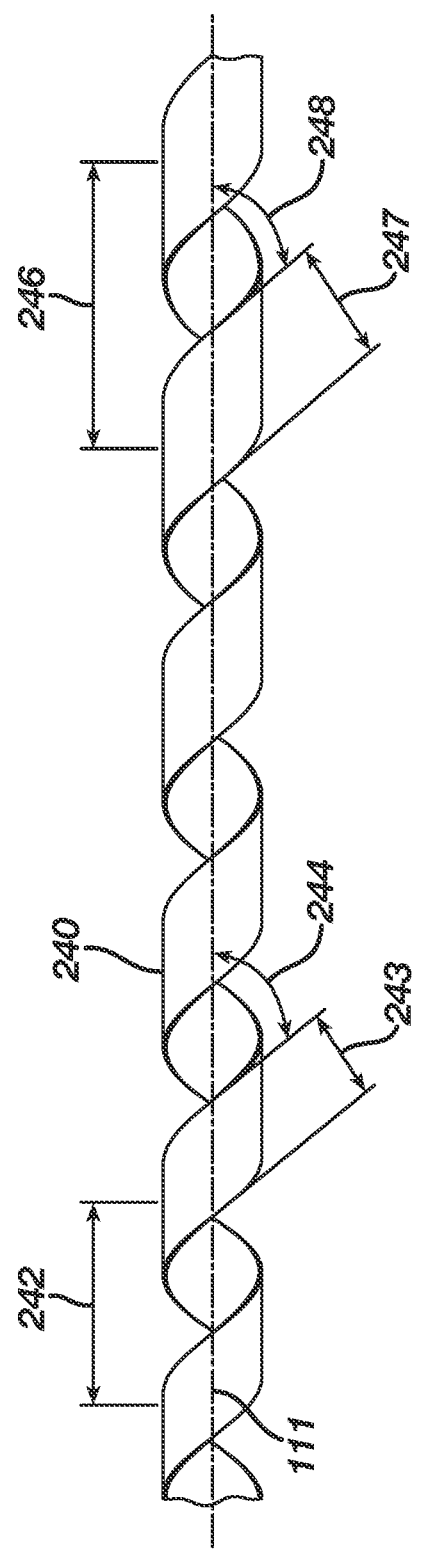
FIG. 6 depicts a ribbon cut segment for the metallic tubular reinforcing layer according to aspects of the present invention.

FIG. 6 shows an example of a section of the ribbon cut segment 240 which has a helical arrangement wrapped around the longitudinal axis 111 to provide the segment with specific flexibility advantages. The ribbon cut segment 240 can be cut so that the helix pitch and coil width are varied along the axial length of the segment. For instance, a first helix pitch 242 can be shortened or increased over a second helix pitch 246. Likewise, ribbon segment 240 can have a second coil width 247 that is wider than a first coil width 243. As the pitch and width change, the helix angle with the longitudinal axis 111 formed by the ribbon coils must also vary, such that a more proximal first helix angle 244 is more obtuse than a second helix angle 248. It can also be appreciated that parameters such as pitch and coil width can be continuously tapered as cut between the proximal end 212 and distal end 214 of the metallic tubular reinforcing layer 210 to avoid abrupt transitions of stiffness. As a result, a high level of variability can be obtained through cutting the wraps of a single ribbon cut segment than if the pitch, coil width, and helix angle were held constant down the length of the segment.

The design of these features and dimensions can thus be adjusted to provide better trackability, thrust, and torque response nearer the proximal end 212 of the metallic tubular reinforcing layer 210. Similarly, near the distal end 214 of the assembly where flexibility is more of a concern, the ribbon cut segment 240 can have the spacing between turns transition to progressive helix pitches to better optimize those physical capabilities.

During prototype testing of several proposed designs, further features to improve performance were discovered. Where the ribbon cut segment 240 joins proximally with the hole patterns 222, 226, a kink point can potentially develop if the metallic tubular reinforcing layer 210 hypotube accounts for a significant portion of the catheter stiffness. This is due to the stress concentrations which result from the geometric dissimilarities between the laser cut features. If dissimilarities are sharp enough at these locations, the metal ribbon cut segment 240 can cut into the outer polymer jacket and cause it to split and/or separate from the construction. Furthermore, even with corner radii, cracks can form at the corners at the extreme proximal end of the ribbon cut segment 240 where the metal hypotube transitions to solid metal with a corresponding hole pattern. Although the ribbon cut segment 240 can have a continuous taper (the metal ribbon width gradually becomes larger in the proximal direction) the jump from ribbon to hole pattern can potentially be too abrupt to avoid a kink/fracture point.

Figure 7A:
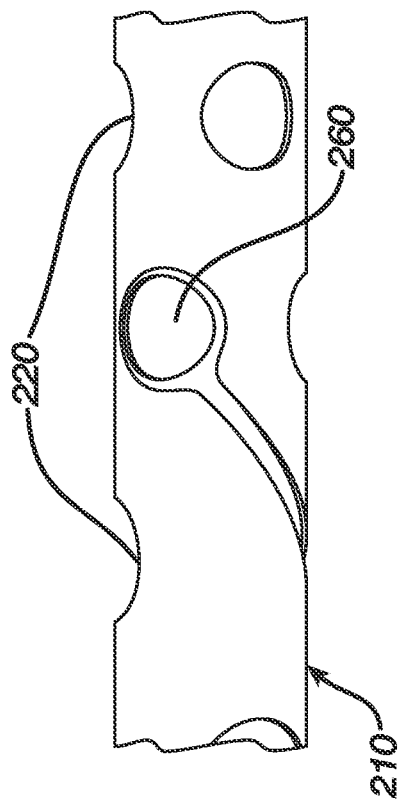
FIGS. 7A-B illustrates possible examples of transition features for the metallic tubular reinforcing layer according to aspects of the present invention.
Figure 7B:
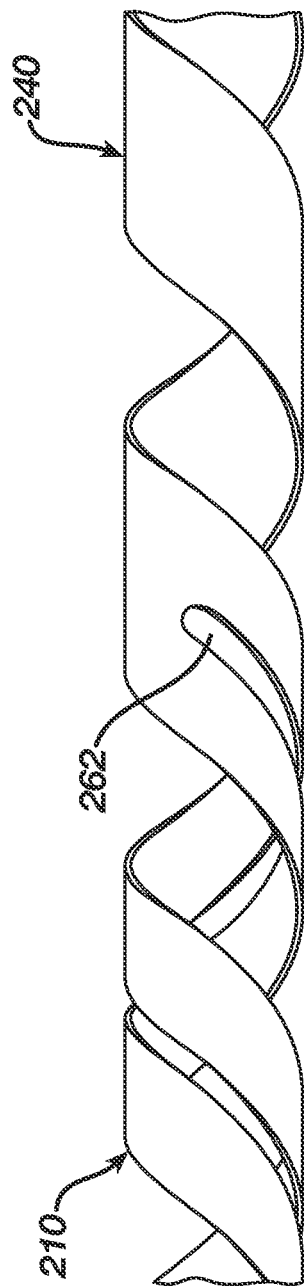

FIGS. 5 and 7A-7B demonstrate that transition features easily incorporated into the designs can prevent force concentration from the ribbon segment to hole configuration during compressive and flexural loads. The concentrations can be more severe if the amount of material cut out to create the ribbon segment 240 is constant (distal to proximal within the ribbon segment). The objective of the transition features can therefore be to provide a better and more flexible transition between the ribbon section of the hypotube and the holed section by allowing additional freedom of motion.

In the example shown, the proximal termination of the ribbon cut segments 240 can evolve into a more solid hypotube of the metallic tubular reinforcing layer 210 through the inclusion of one or more transition holes 260. The transition holes 260 can commence at the proximal cessation of the cuts between ribbon coils, as illustrated in FIG. 5 and FIG. 7A, such that material is removed to aid in flexibility but not in a continuous fashion around the circumference of the tube. This pattern allows for similar material removal to that used to form to the ribbon cut segment 240, but with some material now left (the metal spaces in between the cut holes). The transition holes 260 can also form part of a second hole pattern 226, since the more geometric first hole pattern 222 need not necessarily start immediately after the ribbon segment 240 is complete.

Similarly, once the ribbon cut segment 240 reaches a larger, more proximal second coil width 247 greater than a target width, a spiral cut slot 262 transition feature can be made within the remaining proximal metal ribbon, as illustrated in FIG. 5 and FIG. 7B. This allows some freedom of motion for the wider ribbon sections but not so much that the section loses the greater flexural stiffness profile within the ribbon segment 240 (this section can behave less like a ribbon and becomes more like a solid body, as shown in FIG. 5).

Figure 8:
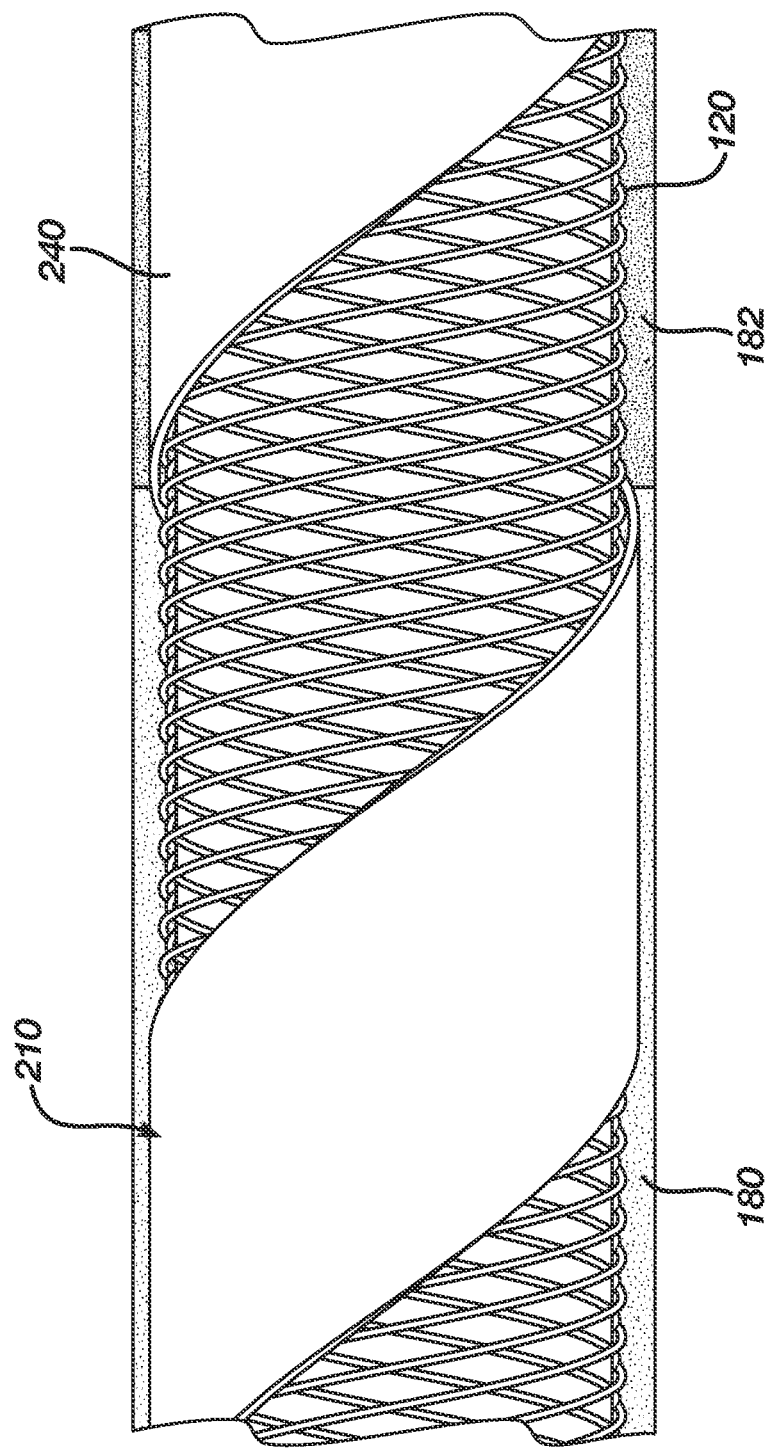
FIG. 8 is a closer view of one of the outer polymer jacket transitions of FIG. 1 according to aspects of the present invention.

As mentioned, multiple outer polymer jackets can be combined to form the outer layer of the catheter 100. A closer view of the transition from a more proximal first polymer jacket 180 to a second polymer jacket 182 of the example shown in FIG. 1 is depicted in FIG. 8. The use of a laser cut metallic tubular reinforcing layer 210 to manage stiffness transitions within the catheter shaft can mean that less reliance is placed on the material properties of the various polymer jackets. Current catheter designs are often limited to polymer durometer transitions that are similar in value in order to relieve the propensity of kinking at such junctions. The metallic tubular reinforcing layer 210 can thus simplify catheter construction and assembly due to decreasing the number of components, allowing a greater disparity between the hardness of first jacket 180 and second jacket 182. Designs incorporating the metallic tubular reinforcing layer 210 can also utilize one to two polymer segments, whereas other current designs can entail the use of up to 12 polymer segments to provide adequate transitions along the longitudinal length and prevent kinking between segments. The disclosed designs can thus use fewer jackets along the length of the catheter shaft, thereby eliminating some of the butt junctions between different durometer jackets.

The outer polymer jackets 180, 182 can be made of various medical grade polymers, such as PTFE, polyether block amide (Pebax®), or Nylon. Materials can be chosen, for example, so that more proximal segments are generally harder and less flexible (by durometer hardness, flexure modulus, etc.) as the proximal end 112 is approached to add column strength and pushability to the catheter. Similarly, more flexible segments can be used distally.

As with other examples, the second polymer jacket 182 can be reflowed on top of the underlying structure. Since it encompasses the desirably more flexible distal portion of the catheter shaft, the second polymer jacket 182 can be a softer material than that used for the first polymer jacket 180. In one example, the second jacket 182 can be a low durometer Pebax® (25D-40D). In another example, the second jacket 182 can be a low durometer urethane or NeuSoft™ (42-73 Shore A). Transitions between jackets can also be tapered or slotted to give a more seamless transition between the flexibility profile of abutting jackets in a longitudinal series.

Figure 9:
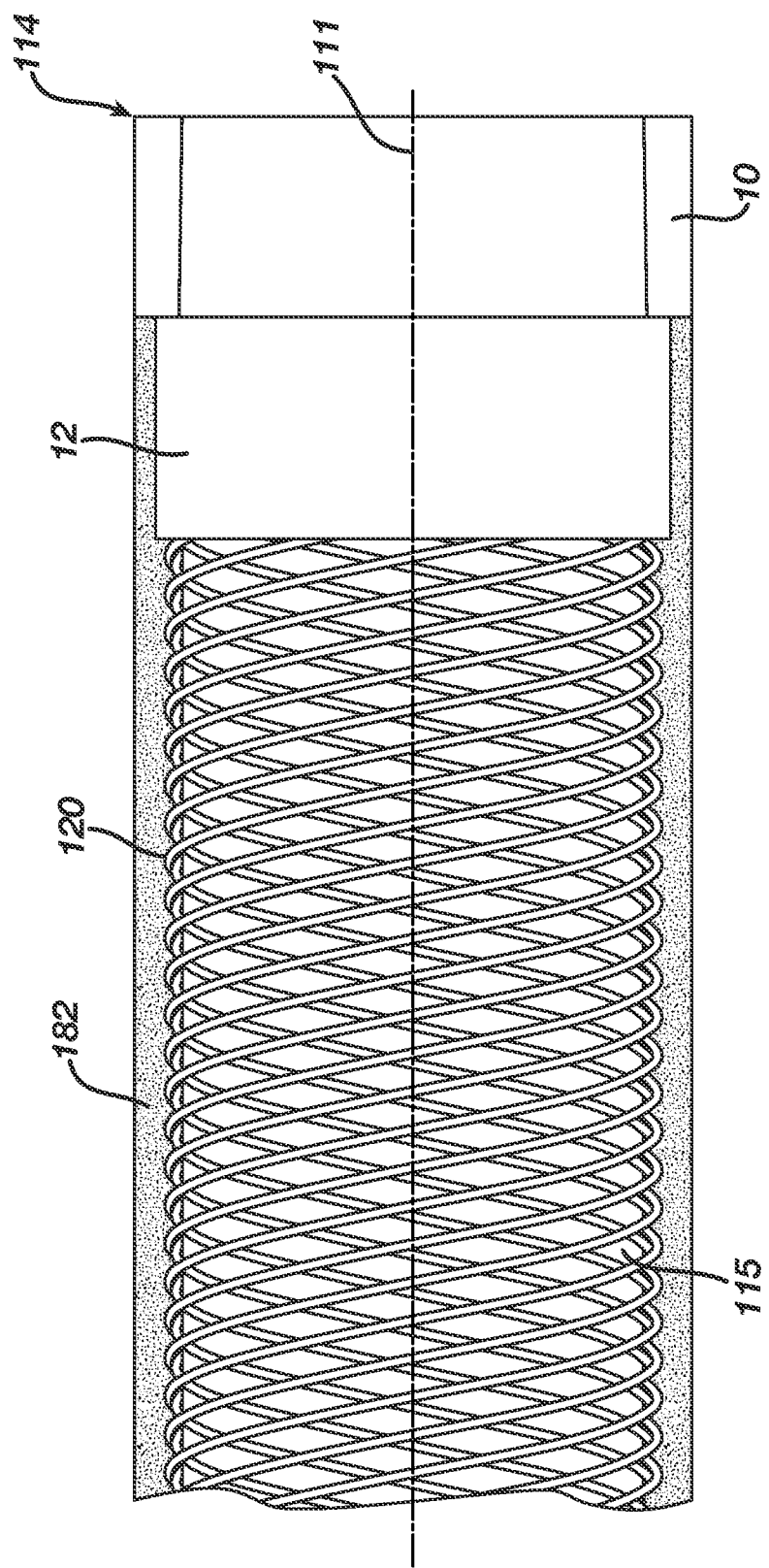
FIG. 9 is a closer view of the distal end of the catheter of FIG. 1 according to aspects of the present invention.

The braided wire support structure 120 can continue distal of the ribbon cut segment 240 to terminate near the distal end 114 of the catheter 100 as shown in FIG. 9. As a result, there can be a distal portion of the catheter with layers of only the inner liner 115, the braided wire support structure 120, and the second polymer jacket 182. A radiopaque marker band, which can be platinum or other suitable material, can be crimped or otherwise connected to mark the terminal distal end 114 of the catheter 100 during a procedure. The distal end can have a very soft polymeric tip 10 around the inner liner 115 and longitudinal axis 111. The tip 10 can be NeuSoft™ or other suitable engineered thermoplastic material which has good elasticity and abrasion resistance while providing UV stability and barrier properties against moisture and oxygen. Though such materials typically have standard durometers from 42-73 Shore A, this range can be extended to meet design specifications through formulation.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

What is claimed is:

1. A catheter comprising:
a proximal end, a distal end, and a longitudinal axis;
an inner liner;
a braided wire support structure disposed around the inner liner;
a metallic tubular reinforcing layer disposed around the braided wire support structure, the metallic tubular reinforcing layer extending an intermediate distance from the proximal end and comprising one or more axial segments configured to give different stiffness properties to at least a portion of the catheter;
a transition feature between a proximal-most ribbon cut segment and a distal-most axial segment of the one or more axial segments comprising one or more axial holes in a first axial hole pattern, the transition feature comprising one or more transition holes in a second axial hole pattern located between the ribbon cuts; and
a plurality of outer polymer jackets disposed around the metallic tubular reinforcing layer, the plurality of outer polymer jackets bonding the metallic tubular reinforcing layer to the braided wire support structure;
at least one of the one or more axial segments of the metallic tubular reinforcing layer comprising one or more ribbon cut segments configured in a continuous longitudinally extending spiral around the longitudinal axis; and
another of the at least one of the one or more axial segments of the metallic tubular reinforcing layer comprising one or more axial hole patterns cut from the metallic tubular reinforcing layer.

2. The catheter of claim 1, the catheter further comprising a soft polymeric tip extending distally from a termination of the braided wire support structure.

3. The catheter of claim 1, wherein the metallic tubular reinforcing layer is cut from a single continuous hypotube.

4. The catheter of claim 1, wherein each of the one or more axial hole patterns comprises at least two holes cut in a radial plane.

5. The catheter of claim 1, wherein at least one proximal ribbon cut segment comprises a spiral cut slot.

6. The catheter of claim 1, wherein the second axial hole pattern is different from the first axial hole pattern and/or is different from a pattern of the one or more axial hole patterns.

7. The catheter of claim 1, wherein at least one of the one or more transition holes is located at a proximal cessation of the cuts between ribbon coils.

8. The catheter of claim 1, wherein at least one of the one or more axial hole patterns comprises a gradient of varying hole density.

9. The catheter of claim 1, wherein at least one of the one or more axial hole patterns comprises holes of differing diameters.

10. The catheter of claim 1, wherein at least one of the one or more axial hole patterns comprises a helical spiral pattern around the longitudinal axis.

11. The catheter of claim 10, wherein the helical spiral pattern comprises an axial portion with a first helix pitch different than a second helix pitch of another axial portion of the helical spiral pattern; and
wherein the helical spiral pattern comprises an axial portion with a first helix angle different than a second helix angle of another axial portion of the helical spiral pattern.

12. The catheter of claim 1, wherein:
at least one of the one or more ribbon cut segments comprises an axial portion with a first ribbon width different than a second ribbon width of another axial portion of the same ribbon cut segment;
wherein at least one of the one or more ribbon cut segments comprises an axial portion with a first helix pitch different than a second helix pitch of another axial portion of the same ribbon cut segment; or
wherein at least one of the one or more ribbon cut segments comprises an axial portion with a first helix angle different than a second helix angle of another axial portion of the same ribbon cut segment.

13. A catheter for vascular access, the catheter comprising:
a proximal end, a distal end, and a longitudinal axis;
a braided wire support structure disposed around an inner liner, the support structure extending from the proximal end of the catheter to a point approximate the distal end;
a metallic tubular reinforcing layer disposed around the braided wire support structure, the metallic tubular reinforcing layer extending an intermediate distance from the proximal end, the metallic tubular reinforcing layer comprising a portion with one or more axial hole patterns cut from the layer having a gradient of varying hole density and a portion with one or more ribbon cut segments configured in a continuous longitudinally extending spiral around the longitudinal axis;
a transition feature between a proximal-most ribbon cut segment of the one or more ribbon cut segments and a distal-most end of the portion comprising one or more axial holes in a first axial hole pattern, the transition feature comprising one or more transition holes in a second axial hole pattern located between the ribbon cuts; and
one or more outer polymer jackets disposed around the metallic tubular reinforcing layer, at least one of the one or more outer polymer jackets comprising a durometer hardness different than the durometer hardness of an adjacent polymer jacket.

14. The catheter of claim 13, wherein each of the one or more axial hole patterns comprises at least two holes cut in a radial plane.

15. The catheter of claim 13, wherein at least one proximal ribbon cut segment comprises a spiral cut slot.

16. The catheter of claim 13, wherein the second axial hole pattern is different from the first axial hole pattern and/or is different from a pattern of the one or more axial hole patterns.

17. The catheter of claim 16, wherein at least one of the one or more transition holes is located at a proximal cessation of the cuts between ribbon coils.

18. The catheter of claim 13, wherein the one or more outer polymer jackets bond the metallic tubular reinforcing layer to the braided wire support structure by flowing through the holes of the one or more axial hole patterns and gaps in the ribbon cut segments when heat is applied.

19. The catheter of claim 18, wherein the helical spiral pattern comprises an axial portion with a first helix pitch different than a second helix pitch of another axial portion of the helical spiral pattern; and wherein the helical spiral pattern comprises an axial portion with a first helix angle different than a second helix angle of another axial portion of the helical spiral pattern.

20. The catheter of claim 13, wherein:
at least one of the one or more ribbon cut segments comprises an axial portion with a first ribbon width different than a second ribbon width of another axial portion of the same ribbon cut segment;
wherein at least one of the one or more ribbon cut segments comprises an axial portion with a first helix pitch different than a second helix pitch of another axial portion of the same ribbon cut segment; or
wherein at least one of the one or more ribbon cut segments comprises an axial portion with a first helix angle different than a second helix angle of another axial portion of the same ribbon cut segment.

* * * * *